United States Patent
Yagihashi et al.

(10) Patent No.: US 11,352,307 B2
(45) Date of Patent: Jun. 7, 2022

(54) CATALYST, DEVICE FOR MANUFACTURING CONJUGATED DIENE, AND METHOD FOR MANUFACTURING CONJUGATED DIENE

(71) Applicant: SEKISUI CHEMICAL CO., LTD., Osaka (JP)

(72) Inventors: Noritoshi Yagihashi, Ibaraki (JP); Toshihito Miyama, Ibaraki (JP); Shinsuke Watanabe, Ibaraki (JP); Haruka Nishiyama, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 16/645,938

(22) PCT Filed: Sep. 27, 2018

(86) PCT No.: PCT/JP2018/036146
§ 371 (c)(1),
(2) Date: Mar. 10, 2020

(87) PCT Pub. No.: WO2019/065924
PCT Pub. Date: Apr. 4, 2019

(65) Prior Publication Data
US 2020/0199045 A1    Jun. 25, 2020

(30) Foreign Application Priority Data

Sep. 27, 2017   (JP) ............... JP2017-186533

(51) Int. Cl.
| | | |
|---|---|---|
| *B01J 23/10* | (2006.01) |
| *B01J 21/06* | (2006.01) |
| *B01J 23/06* | (2006.01) |
| *C07C 1/20* | (2006.01) |
| *C07C 6/10* | (2006.01) |
| *C07C 11/167* | (2006.01) |

(52) U.S. Cl.
CPC ............... *C07C 1/20* (2013.01); *B01J 21/066* (2013.01); *B01J 23/06* (2013.01); *B01J 23/10* (2013.01);
(Continued)

(58) Field of Classification Search
None
See application file for complete search history.

(56) References Cited

U.S. PATENT DOCUMENTS

| | | | | |
|---|---|---|---|---|
| 8,975,424 B1 * | 3/2015 | Suchanek | ............... | B01J 23/66 549/536 |
| 2013/0023709 A1 * | 1/2013 | Cizeron | ............... | B01J 19/0046 585/324 |

(Continued)

FOREIGN PATENT DOCUMENTS

| | | |
|---|---|---|
| CN | 106824259 | 6/2017 |
| EP | 3 090 801 | 11/2016 |

(Continued)

OTHER PUBLICATIONS

International Search Report dated Dec. 18, 2018 in International (PCT) Application No. PCT/JP2018/036146.

(Continued)

*Primary Examiner* — Philip Y Louie
*Assistant Examiner* — Alyssa L Cepluch
(74) *Attorney, Agent, or Firm* — Wenderoth, Lind & Ponack, L.L.P.

(57) ABSTRACT

A catalyst for synthesizing a conjugated diene from a raw material including an alcohol, which includes at least Ce and Zn as metal elements constituting the catalyst. An apparatus for producing a conjugated diene, including: a reaction tube (1) provided with the catalyst; a supply means for supplying a raw material gas containing the raw material into the reaction tube (1); and an outlet means for releasing a product (Continued)

from the reaction tube (1). A method for producing a conjugated diene, including contacting a raw material gas containing a raw material with the catalyst to obtain a conjugated diene. The amount of the raw material is preferably 10 to 50% by volume (in terms of gas volume) with respect to 100% by volume (in terms of gas volume) of the raw material gas.

7 Claims, 1 Drawing Sheet

(52) U.S. Cl.
CPC .............. *C07C 6/10* (2013.01); *C07C 11/167* (2013.01); *C07C 2521/06* (2013.01); *C07C 2523/06* (2013.01); *C07C 2523/10* (2013.01)

(56) References Cited

U.S. PATENT DOCUMENTS

| | | | |
|---|---|---|---|
| 2013/0211148 A1 | 8/2013 | Schäfer et al. | |
| 2018/0208522 A1 | 7/2018 | Cadran et al. | |

FOREIGN PATENT DOCUMENTS

| | | |
|---|---|---|
| JP | 2013-177380 | 9/2013 |
| JP | 2015-168644 | 9/2015 |
| JP | 2017-144359 | 8/2017 |
| WO | 2014/129248 | 8/2014 |
| WO | 2014/199349 | 12/2014 |
| WO | 2017/009107 | 1/2017 |

OTHER PUBLICATIONS

De Baerdemaeker et al., "Bimetallic Zn and Hf on Silica Catalysts for the Conversion of Ethanol to 1,3-Butadiene", ACS Catalysis, vol. 5, Apr. 24, 2015, pp. 3393-3397.

Extended European Search Report dated May 31, 2021 in European Patent Application No. 18861398.8.

Apostolescu et al., "Studies on the Photocatalytic Degradation of Organic Dyes Using $CeO_2$—ZnO Mixed Oxides", Environmental Engineering and Management Journal, Feb. 2015, vol. 14, No. 2, pp. 415-420.

* cited by examiner

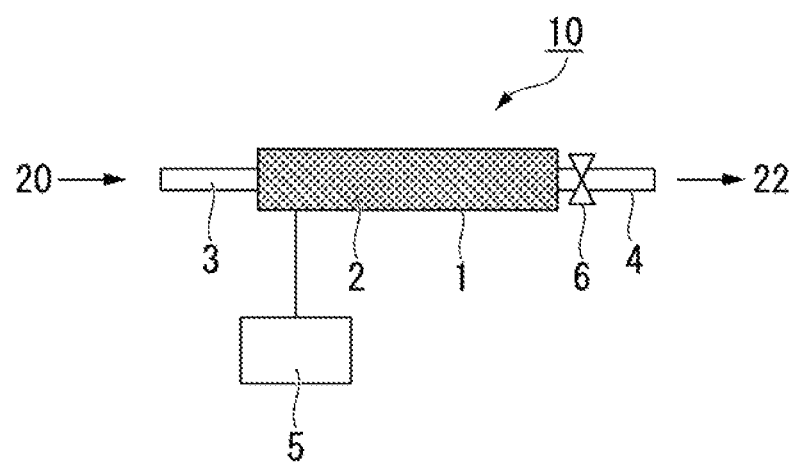

CATALYST, DEVICE FOR MANUFACTURING CONJUGATED DIENE, AND METHOD FOR MANUFACTURING CONJUGATED DIENE

TECHNICAL FIELD

The present invention relates to a catalyst, an apparatus for producing a conjugated diene, and a method for producing a conjugated diene.

Priority is claimed on Japanese Patent Application No. 2017-186533, filed Sep. 27, 2017, the contents of which are incorporated herein by reference.

BACKGROUND ART

Butadiene such as 1,3-butadiene is used as a raw material for styrene-butadiene rubber (SBR) and the like. Conventionally, butadiene has been purified from the C4 fraction. The C4 fraction is a fraction obtained as a by-product during naphtha cracking for producing ethylene from petroleum. However, the use of petroleum has decreased as a result of increased use of shale gas. Consequently, the butadiene production by naphtha cracking of petroleum has also decreased. Therefore, there is a need for an alternative method for producing 1,3-butadiene.

As an example of method for producing 1,3-butadiene, production by oxidative dehydrogenation reaction of 1-butene as a raw material can be listed. However, in this method, 1-butene which is difficult to separate from 1,3-butadiene remains in the product. This makes the purification process complicated, and makes the production economically inferior.

In recent years, chemical engineering materials derived from biomass-derived materials have been receiving attention instead of chemical engineering materials obtained from petroleum. In the case of 1,3-butadiene and the like as well, the importance of production from bioethanol derived from biomass such as sugarcane and corn has been increasing.

Patent Documents 1 to 3 disclose a method for producing butadiene in which a raw material gas containing ethanol is brought into contact with a catalyst.

The catalyst used in the invention of Patent Document 1 contains Hf and two or more kinds of catalytically active metals selected from Zr, Zn, and Cu.

The catalyst used in the invention of Patent Document 2 has a magnesium silicate structure.

The catalyst used in the invention of Patent Document 3 contains germanium oxide and magnesium oxide.

DESCRIPTION OF PRIOR ART

Patent Document

Patent Document 1: International Patent Application Publication No. 2014/199349
Patent Document 2: Japanese Unexamined Patent Application Publication No. 2015-168644
Patent Document 3: International Patent Application Publication No. 2014/129248

DISCLOSURE OF INVENTION

Problems to be Solved by the Invention

However, although the inventions of Patent Documents 1 and 2 can increase the selectivity of butadiene, it is necessary to lower the ethanol concentration in the raw material gas. Therefore, in the inventions of Patent Documents 1 and 2, the yield of butadiene per unit time is small, and it is difficult to increase the production efficiency of butadiene.

In the invention of Patent Document 3, although the concentration of ethanol in the raw material gas can be increased, it is necessary to use a raw material gas containing ethanol and hydrogen. For this reason, in the invention of Patent Document 3, the handling of the raw materials is complicated, and the production according to this invention is economically inferior. As a result, it is difficult to increase the production efficiency.

For addressing these problems, the present invention aims at providing a catalyst for synthesizing a conjugated diene, which is capable of increasing the production efficiency of a conjugated diene from a raw material containing an alcohol.

Means to Solve the Problems

The embodiments of the present invention are as follows.
[1] A catalyst for synthesizing a conjugated diene from a raw material comprising an alcohol, which comprises at least Ce and Zn as metal elements constituting the catalyst.
[2] The catalyst according to [1], which further includes at least one metal element A selected from metal elements belonging to Group 4 of the periodic table as metal element constituting the catalyst.
[3] The catalyst according to [1] or [2], wherein the metal element A is Hf.
[4] The catalyst according to any one of [1] to [3], wherein the alcohol is ethanol.
[5] The catalyst according to any one of claims [1] to [4], which is a catalyst for synthesizing a conjugated diene.
[6] The catalyst according to [1], wherein the raw material further includes acetaldehyde.
[7] The catalyst according to [1] or [2], wherein the metal elements are supported on a carrier.
[8] The catalyst according to any one of [1] to [7], which satisfies formula (I):

$$A_x Zn_y Ce_z \qquad (I)$$

wherein A represents a metal element A belonging to Group 4 of the periodic table, and x, y, and z are numbers representing mass ratios of the metal elements A, Zn, and Ce, respectively, provided that:
x is 0 to 10,
y is from 0.1 to 5, and
z is 0.5 to 20.
[9] The catalyst according to [8], wherein in the formula (I), x is 0.5 to 10, y is 0.1 to 5, and z is 0.5 to 20.
[10] An apparatus for producing a conjugated diene, including: a reaction tube provided with the catalyst of any one of [1] to [9]; a supply means for supplying a raw material gas containing the raw material into the reaction tube; and an outlet means for releasing a product from the reaction tube.
[11] The apparatus according to [10], wherein the conjugated diene is butadiene.
[12] A method for producing a conjugated diene, including contacting a raw material gas containing a raw material with the catalyst of any one of [1] to [9] to obtain a conjugated diene.
[13] The method according to [11], wherein the conjugated diene is butadiene.

[14] The method according to [12], wherein the amount of the raw material is 10 to 50% by volume (in terms of gas volume) with respect to 100% by volume (in terms of gas volume) of the raw material gas.
[15] The method according to any one of [12] to [14], wherein the raw material gas is a mixed gas of the raw material and an inert gas.
[16] A conjugated diene obtained by the method of any one of [12] to [15].

Effect of the Invention

The catalyst of the present invention can increase the production efficiency of a conjugated diene.

BRIEF DESCRIPTION OF THE DRAWINGS

The FIG is a schematic view of the apparatus for producing a conjugated diene according to one embodiment of the present invention.

DESCRIPTION OF THE EMBODIMENTS

Throughout the specification and claims, the following terms should be understood as defined below.

The terms "conjugated diene selectivity" (butadiene selectivity, etc.) means the percentage of the number of moles of the raw material converted to conjugated diene (butadiene etc.) out of the number of moles of the raw material consumed in the reaction using the synthesis catalyst. When only ethanol is used as the raw material, the number of moles of the raw material is the number of moles of ethanol. When both ethanol and acetaldehyde are used as the raw materials, the number of moles of the raw materials is the total number of moles thereof.

The term "raw material conversion" means the percentage of the number of moles of the raw material consumed relative to the moles of the raw material contained in the raw material gas.

Further, "to" indicating a numerical range means that the numerical values described before and after "to" are included as the lower limit and the upper limit of the range.

The use of (synthesis reaction to be catalyzed by) the catalyst described in the present specification (hereinafter also referred to simply as "synthesis catalyst") is not particularly limited, but the catalyst is preferably a synthesis catalyst for producing conjugated diene, and more preferably a synthesis catalyst for producing butadiene.
(Synthesis Catalyst)

The synthesis catalyst of the present invention is a catalyst for synthesizing a conjugated diene from the raw material. The conjugated diene is not particularly limited, but is preferably butadiene (1,3-butadiene).

The raw material for synthesizing the conjugated diene includes at least alcohol, preferably ethanol. Further, the raw material may contain acetaldehyde as well.

The synthesis catalyst of the present invention is a catalyst including at least Ce (cerium) and Zn (zinc), and preferably further includes a metal element A belonging to Group 4 of the periodic table. The metal element A includes Hf (hafnium), Zr (zirconium), and Ti (titanium). Of these, Hf is preferable because of its low electronegativity. These elements may be present as a metal or a compound in the catalyst.

The synthesis catalyst of the present invention can increase the production efficiency of a conjugated diene, preferably butadiene.

The synthesis catalyst preferably has a composition satisfying formula (I):

$$A_xZn_yCe_z \qquad (I)$$

wherein A represents a metal element A belonging to Group 4 of the periodic table, and x, y, and z are numbers representing mass ratios of the metal elements A, Zn, and Ce, respectively, provided that:
x is 0 to 10,
y is from 0.1 to 5, and
z is 0.5 to 20.

In the formula (I), x is generally 0 to 10, preferably 0.5 to 10, more preferably 1 to 5, and even more preferably 2 to 4. When x is within the above range, the selectivity of the conjugated diene, preferably butadiene, is further increased.

In the formula (I), y is generally 0.1 to 5, preferably 0.5 to 2, more preferably 0.75 to 1.75, and even more preferably 1 to 1.5. When y is within the above range, the selectivity of the conjugated diene, preferably butadiene, is further increased.

In the formula (1), z is generally 0.5 to 20, preferably 1 to 15, and more preferably 2 to 10. When z is within the above range, the selectivity of the conjugated diene, preferably butadiene, is further increased.

The mass ratio, A/Zn, of the metal element A to the metal element Zn is not particularly limited, but is usually 0 to 8/1, preferably 1/1 to 6/1, and more preferably 2/1 to 4/1. When the ratio of the metal element A to the metal element Zn is not less than the lower limit described above, the raw material conversion is further increased. When the ratio of the metal element A to the metal element Zn is not more than the upper limit described above, the selectivity of conjugated diene, preferably butadiene, is further increased.

The mass ratio, Ce/metal element A, is preferably 1/6 to 10/1, and more preferably 1/3 to 3/1. When this ratio Ce/metal element A is not less than the lower limit described above, the selectivity of conjugated diene, preferably butadiene, is further increased. When the ratio Ce/metal element A is not more than the upper limit described above, the raw material conversion is further increased.

The mass ratio, Ce/Zn, is preferably 1/2 to 20/1, and more preferably 1/1 to 10/1. When this ratio Ce/Zn is not less than the lower limit described above, the selectivity of conjugated diene, preferably butadiene, is further increased. When this ratio Ce/Zn is not more than the upper limit described above, the selectivity of conjugated diene, preferably butadiene, is further increased.

The catalyst metals may include a metal other than Hf, Zn and Ce as long as the effects of the present invention are not impaired.

The synthesis catalyst may be an aggregate or condensate of the metal elements specified in the present invention, or a supported catalyst in which the metal elements specified in the present invention are supported on a carrier. Preferably, the synthesis catalyst is a supported catalyst in which the metal elements are supported on a carrier.

When the synthesis catalyst is a supported catalyst, a well-known carrier for metal catalysts can be employed as a carrier. The carrier may be, for example, a porous carrier such as silica, titania, and alumina. Among them, silica is preferable as the porous carrier. As for silica, there are various products having different specific surface areas and pore sizes. By combining porous carries of different specific surface areas and pore diameters, the conjugated diene selectivity (such as butadiene selectivity) and the raw material conversion can be controlled.

The size of the porous carrier is not particularly limited. For example, in the case of a porous silica carrier, the particle size of the porous carrier is preferably in the range of 150 to 2,360 μm. The particle size of the porous carrier can be controlled by sifting. The porous carrier is preferably one with a particle size distribution as narrow as possible.

The total of the pore volumes of the porous carrier (total pore volume) is not particularly limited, and is, for example, preferably 0.10 to 2.50 mL/g, and more preferably 0.25 to 1.50 mL/g. When the total pore volume is not less than the lower limit described above, a sufficient amount of the catalyst metals can be easily supported, and the raw material conversion and the conjugated diene selectivity are further increased. When the total pore volume is not more than the upper limit described above, a sufficient contact area between the raw material and the synthesis catalyst is likely to be achieved, and the raw material conversion and the conjugated diene selectivity are further increased.

The total pore volume of the porous carrier is a value measured by the aqueous titration method. In the aqueous titration method, water molecules are adsorbed onto a surface of the porous carrier, and the pore distribution is measured based on the condensation of the molecules.

The average pore diameter of the porous carrier is preferably, for example, 0.1 to 100 nm, and more preferably 1.0 to 50 nm. When the average pore volume is not less than the lower limit described above, a sufficient amount of the catalyst metals can be easily supported, and the raw material conversion and the conjugated diene selectivity are further increased. When the average pore volume is not more than the upper limit described above, a sufficient contact area between the raw material and the synthesis catalyst is likely to be achieved, and the raw material conversion and the conjugated diene selectivity are further increased.

The average pore diameter is a value measured by the following method. When the average pore diameter is 0.1 nm or more and less than 50 nm, the average pore diameter is calculated from the total pore volume and the BET specific surface area. When the average pore diameter is 50 nm or more, the average pore diameter is measured by a mercury porosimeter. The BET specific surface area is a value calculated from an adsorbed amount of nitrogen that is an adsorption gas, and a pressure at the time of adsorption. In the mercury porosimetry, a pressure is applied to inject mercury into pores of the porous carrier, and the average pore diameter is calculated from the pressure and an amount of the mercury injected.

The specific surface area of the porous carrier is preferably 50 to 1000 $m^2/g$, and more preferably 100 to 750 $m^2/g$. When the specific surface area is not less than the lower limit described above, a sufficient supported amount of the catalyst metals tends to be achieved, and the raw material conversion and the conjugated diene selectivity are further increased. When the specific surface area is not more than the upper limit described above, a sufficient contact area between the raw material and the synthesis catalyst is likely to be achieved, and the raw material conversion and the conjugated diene selectivity are further increased.

The specific surface area means the BET specific surface area, which is measured by the BET gas adsorption method using nitrogen as an adsorption gas.

The product of the total pore volume and the specific surface area of the porous carrier is preferably 5 to 7500 $mL \cdot m^2/g^2$, and is more preferably 100 to 5000 $mL \cdot m^2/g^2$. When the product is not less than the lower limit described above, a sufficient supported amount of the catalyst metals tends to be achieved, and the raw material conversion and the conjugated diene selectivity are further increased. When the product is not more than the upper limit described above, a sufficient contact area between the raw material and the synthesis catalyst is likely to be achieved, and the raw material conversion and the conjugated diene selectivity are further increased.

The total amount of the catalyst metals supposed on the porous carrier is preferably 1 to 30% by mass, more preferably 1.1 to 30% by mass, even more preferably 2.5 to 22% by mass, even more preferably 2.5 to 10% by mass, and may be 5 to 15.5% by mass, with respect to 100% by mass of the porous carrier. When the total amount of the supported catalyst metals is not less than the lower limit described above, a sufficient amount of the catalyst metals can be supported, and the raw material conversion and the conjugated diene selectivity are further increased. When the total amount of the supported catalyst metals is not more than the upper limit described above, the catalyst metals can be highly and uniformly dispersed with ease, so that the conjugated diene selectivity can be further increased.

The amount of the metal element A supposed on the porous carrier is generally 0 to 10% by mass, preferably 0.5 to 10% by mass, more preferably 0.6 to 10% by mass, even more preferably 1 to 5% by mass, and particularly preferably 2 to 4% by mass, with respect to 100% by mass of the porous carrier.

The amount of Zn supported on the porous carrier is preferably 0.1 to 5% by mass, more preferably 0.5 to 2% by mass, preferably 0.75 to 1.75% by mass, and particularly preferably 1 to 1.5% by mass, with respect to 100% by mass of the porous carrier.

The amount of Ce supported on the porous carrier is preferably 0.5 to 20% by mass, more preferably 1 to 15% by mass, and even more preferably 2 to 10% by mass, with respect to 100% by mass of the porous carrier.

The synthesis catalyst can be produced following the conventionally known methods for producing catalysts, except that the synthesis catalyst includes at least Ce and Zn, and preferably further includes at least one metal element A selected from metal elements belonging to Group 4 of the periodic table. In the case where the synthesis catalyst is in the form of a supported catalyst, examples of the method for producing the same include an impregnation method, a coprecipitation method, and an ion exchange method.

In the impregnation method, after impregnating a porous carrier with an impregnation liquid, the resulting is dried and calcined to obtain a synthesis catalyst. For example, raw material compounds of catalyst metals are dissolved in a solvent to prepare an impregnation liquid.

The raw material compounds of the catalyst metals are not particularly limited, and compounds generally used in metal catalyst preparation can be used. Examples of the raw material compound include oxides; inorganic salts such as chlorides, sulfides, nitrates and carbonates; organic salts or chelate compounds such as oxalates, acetylacetonate salts, dimethylglyoxime salts and ethylenediamine acetic acid salts; carbonyl compounds; cyclopentadienyl compounds; amine complexes; alkoxide compounds; and alkyl compounds.

Examples of the solvent include water, methanol, ethanol, tetrahydrofuran, dioxane, hexane, benzene, and toluene.

Examples of the method for impregnating the porous carrier with the impregnation liquid include a simultaneous method, a sequential method and the like. The simultaneous method is a method of impregnating a carrier with a solution in which all the raw material compounds are dissolved. The sequential method is a method in which respective solutions of the raw material compounds are separately prepared, and a carrier is sequentially impregnated with the solutions.

The drying temperature and the calcination temperature may be appropriately determined depending on the type of the solvent and the like. For example, when the solvent is water, the drying temperature may be 80 to 120° C., and the calcination temperature may be 300 to 600° C. The drying time and the calcination time may be appropriately determined depending on the drying temperature and the calcination temperature, the type of the solvent, and the like. For example, when the solvent is water, the drying time may be 10 minutes to 24 hours, and the calcination time may be 30 minutes to 100 hours.

(Apparatus for Producing Conjugated Diene)

The apparatus of the present invention for producing a conjugated diene includes a reaction tube filled with the synthesis catalyst of the present invention.

The apparatus of the present invention produces a conjugated diene from a raw material gas containing a raw material.

Hereinbelow, an example of an apparatus for producing butadiene which is one type of the conjugated diene in the present invention is described with reference to the FIG. The butadiene production apparatus 10 of the present embodiment (hereinafter, simply referred to as "production apparatus 10") includes a reaction tube 1, a supply pipe 3, an outlet pipe 4, a temperature controller 5, and a pressure controller 6.

The reaction tube 1 has a reaction bed 2 inside. The reaction bed 2 is packed with the synthesis catalyst of the present invention. The supply pipe 3 is connected to the reaction tube 1. The outlet pipe 4 is connected to the reaction tube 1. The temperature controller 5 is connected to the reaction tube 1. The outlet pipe 4 is equipped with a pressure controller 6.

The reaction bed 2 may have only the synthesis catalyst of the present invention, or may have a diluent as well as the synthesis catalyst of the present invention. The diluent prevents the catalyst from generating excessive heat.

Here, the reaction for synthesizing butadiene from the raw material is an endothermic reaction. For this reason, the reaction bed 2 usually does not require a diluent.

The diluent may be, for example, the same as in the carrier of the synthetic catalyst, quartz sand, alumina balls, aluminum balls, aluminum shots, and the like.

When a diluent is charged into the reaction bed 2, the mass ratio, diluent/synthesis catalyst, is determined in consideration of the type, specific gravity and the like of the diluent and the synthesis catalyst, and is, for example, preferably 0.5 to 5.

The reaction bed may be any of a fixed bed, a moving bed, a fluidized bed, and the like.

The reaction tube 1 is preferably made of a material that is inert to the raw material gas and the synthesized product. The reaction tube 1 preferably has a shape that enables the reaction tube 1 to withstand heating at about 100 to 500° C. or pressurization at about 10 MPa. The reaction tube 1 may be, for example, a substantially cylindrical member made of stainless steel.

The supply pipe 3 is a supply means that supplies the raw material gas into the reaction pipe 1. The supply pipe 3 is, for example, a pipe made of stainless steel.

The outlet pipe 4 is an outlet means that releases a gas containing a product synthesized in the reaction bed 2. The outlet pipe 4 is, for example, a pipe made of stainless steel or the like.

With respect to the temperature controller 5, there is no particular limitation as long as it can control the temperature of the reaction bed 2 in the reaction tube 1 to a desired value. For example, the temperature controller 5 may be an electric furnace or the like.

With respect to the pressure controller 6, there is no particular limitation as long as it can control the internal pressure of the reaction tube 1 to a desired value. For example, the pressure controller 6 may be a known pressure valve or the like.

The production apparatus 10 may be equipped with a known device such as a gas flow rate controller (e.g., mass flow controller) or the like which adjusts a flow rate of the gas.

(Method for Producing Conjugated Diene)

The method of the present invention for producing a conjugated diene is a method for producing a conjugated diene from a raw material using the above-described synthesis catalyst of the present invention. In the present invention, the conjugated diene to be produced is not particularly limited, but is preferably butadiene (1,3-butadiene).

In the method for producing a conjugated diene, a raw material gas containing a raw material is brought into contact with the synthesis catalyst of the present invention.

The raw material is a substance that can be converted from a raw material containing an alcohol into a conjugated diene, and the main component thereof is preferably an alcohol. The "main component" as used herein means that the component occupies 50% by mass or more of the raw material. Acetaldehyde may be contained in the raw material in addition to the alcohol. Ethanol is preferred as the alcohol.

With respect to the method for bringing the raw material gas into contact with the synthesis catalyst, there is no particular limitation. An example thereof is a method in which the raw material gas is passed through the reaction bed in the reaction tube so as to allow the synthesis catalyst in the reaction bed to contact the raw material gas.

When the raw material contains acetaldehyde, the amount of the alcohol, preferably ethanol, relative to 100% by volume of the raw material, is preferably 50% by volume or more, 55% by volume or more, 60% by volume or more, 65% by volume or more, 70% by volume or more, 75% by volume or more, 80% by volume or more, 90% by volume or more, 95% by volume or more, or 99.9% by volume or more. When the amount of ethanol is less than 50% by volume, the amount of acetaldehyde is excessive, and the production efficiency of the conjugated diene may decrease.

The raw material gas may include a gas (optional gas) other than the above-mentioned raw material. Examples of the optional gas include a hydrogen gas, an oxygen gas, and an inert gas, of which an inert gas such as nitrogen or argon is preferable.

In the present invention, an inert gas is used as a diluent gas. When the raw material gas contains a diluent gas, the butadiene selectivity is further increased.

The amount of the raw material (hereinafter also referred to as "raw material concentration") may be 100% by volume (in terms of gas volume) with respect to 100% by volume (in terms of gas volume) of the raw material gas. However, the raw material concentration is preferably from 10 to 70% by volume, more preferably from 10 to 50% by volume, and even more preferably from 20 to 40% by volume. When the raw material concentration is not less than the lower limit described above, the yield of butadiene per unit time is further increased. When the raw material concentration is not more than the upper limit described above, the butadiene selectivity is further increased.

When the raw material gas contains an inert gas, the amount of the inert gas is preferably 30 to 90% by volume, more preferably 50 to 90% by volume, and even more preferably 60 to 80% by volume, with respect to 100% by volume of the raw material gas. When the amount of the inert gas is not less than the lower limit described above, the butadiene selectivity is further increased. When the amount of the inert gas is not more than the upper limit described above, the yield of butadiene per unit time is further increased.

The temperature (reaction temperature) at which the raw material gas is brought into contact with the synthesis catalyst is preferably from 300 to 500° C., and more preferably from 350 to 450° C. When the reaction temperature is not lower than the lower limit described above, the reaction rate is sufficiently increased, and butadiene can be produced more efficiently. When the reaction temperature is not higher than the upper limit described above, deterioration of the synthesis catalyst is easily suppressed.

The pressure (reaction pressure) at which the raw material is brought into contact with the synthesis catalyst is, for example, preferably 0.1 to 10 MPa, and more preferably 0.1 to 3 MPa. When the reaction pressure is not lower than the lower limit described above, the reaction rate is sufficiently increased, and butadiene can be produced more efficiently. When the reaction pressure is not higher than the upper limit described above, deterioration of the synthesis catalyst is easily suppressed.

The space velocity (SV) of the raw material gas in the reaction bed is preferably 0.1 to 10000 L/h/L-catalyst, more preferably from 10 to 5000 L/h/L-catalyst, and even more preferably from 100 to 2500 L/h/L-catalyst, in terms of the value under the standard condition. The space velocity is appropriately adjusted in consideration of the reaction pressure and the reaction temperature.

For example, when butadiene is produced using the production apparatus 10, the temperature controller 5 and the pressure controller 6 adjust the internal temperature and pressure of the reaction tube 1 to the respective predetermined values. The raw material gas 20 is supplied from the supply pipe 3 into the reaction tube 1. In the reaction tube 1, the raw material comes into contact with the synthesis catalyst and reacts to generate butadiene. The product gas 22 containing butadiene is released from the outlet pipe 4.

The product gas 22 may contain compounds such as acetaldehyde, propylene, and ethylene.

With respect to the product gas 22 containing butadiene, the product gas is subjected to purification such as gas-liquid separation or distillation purification as necessary to remove unreacted raw materials and by-products.

According to the present invention, the use of the specific synthesis catalyst enables a conjugated diene to be produced with a higher raw material conversion and a higher selectivity of a conjugated diene, preferably butadiene. In addition, according to the present invention, the raw material concentration in the raw material gas can be increased, so that the yield of the conjugated diene per unit time can be increased. Furthermore, an inert gas can be used as a diluent gas, which allows for easy handling of the raw material gas. Therefore, the present invention can increase the production efficiency of the conjugated diene.

It is also particularly to be noted that the present invention enables the production of butadiene from bioethanol to thereby reduce the environmental burden.

EXAMPLES

Hereinbelow, the present invention will be described with reference to Examples which, however, should not be construed as limiting the present invention.

Experimental Examples 1 to 9

In "Catalyst composition" in Table 1, the numerical value next to each element symbol indicates the amount of the element supported on the carrier (% by mass) relative to 100% by mass of the porous carrier. For example, "Hf3Zn1Ce5" of Experimental Example 1 indicates that 3% by mass of Hf, 1% by mass of Zn, and 5% by mass of Ce are supported on the porous carrier with respect to 100% by mass of the porous carrier. Further, "Hf0Zn1Ce5" of Experimental Example 7 indicates that 1% by mass of Zn and 5% by mass of Ce are supported while Hf is not supported.

Hafnium (IV) chloride, zinc nitrate hexahydrate, and cerium nitrate hexahydrate were dissolved in water so as to provide a composition of the catalyst metals as shown in Table 1, to thereby obtain an impregnation liquid. This impregnation liquid was applied to a porous carrier (silica, particle diameter: 1.18 to 2.36 mm, average pore diameter: 10 nm, total pore volume: 1.01 mL/g, specific surface area: 283 m$^2$/g). This porous product was dried at 110° C. for 3 hours, and further calcined at 400° C. for 4.5 hours to obtain a synthesis catalyst to be used in the Examples.

Butadiene was produced using the obtained synthesis catalysts, and the results are shown in Table 1.

Experimental examples 1 to 7 are the examples of the present invention.

Experimental Example 10

A synthesis catalyst of Experimental Example 10 was obtained in the same manner as in Experimental Example 1, except that copper nitrate trihydrate was used instead of cerium nitrate hexahydrate.

Butadiene was produced using the obtained synthesis catalyst, and the results are shown in Table 1.

(Evaluation Method)

3.4 g of the synthesis catalyst of each of the Examples was filled into a stainless steel cylindrical reaction tube having a diameter of ½ inch (1.27 cm) and a length of 15.7 inch (40 cm) to form a reaction bed.

Next, the reaction temperature (temperature of the reaction bed) was set to 400° C., the reaction pressure (pressure of the reaction bed) was set to 0.1 MPa, and the raw material gas was supplied to the reaction tube with a SV of 1200 L/hr/L-catalyst to obtain a product gas. The raw material gas was a mixed gas of 30% by volume (in terms of gas volume) of ethanol and 70% by volume (in terms of gas volume) of nitrogen. The recovered product gas was analyzed by gas chromatography, and the selectivities of butadiene (1,3-butadiene), acetaldehyde and ethylene and propylene, the raw material conversion, and the butadiene yield were determined. The butadiene yield is a value determined by [raw material conversion]×[butadiene selectivity]. The results are shown in Table 1.

TABLE 1

| Experimental Example No. | Composition of catalyst | Raw material conversion (mol %) | Selectivity (mol %) | | | | Butadiene yield (mol %) |
|---|---|---|---|---|---|---|---|
| | | | Butadiene | Acetaldehyde | Ethylene | Propylene | |
| 1 | Hf3Zn1Ce5 | 96.9 | 65.1 | 4.6 | 6.3 | 4.1 | 63 |
| 2 | Hf1Zn1Ce5 | 87.1 | 57.1 | 10.7 | 3.3 | 3.7 | 50 |
| 3 | Hf5Zn1Ce5 | 96 | 54.8 | 6.8 | 4.5 | 3.7 | 53 |
| 4 | Hf3Zn0.5Ce5 | 93.1 | 59.7 | 5 | 7.4 | 3.6 | 56 |
| 5 | Hf3Zn2Ce5 | 962 | 59.6 | 9.4 | 3.2 | 4.2 | 57 |
| 6 | Hf3Zn1Ce1 | 97.1 | 59 | 8.3 | 3.3 | 4.3 | 57 |
| 7 | Hf0Zn1Ce5 | 56.2 | 14.4 | 59.5 | 7.8 | 2.8 | 8 |
| 8 | Hf3Zn0Ce5 | 30.5 | 2.5 | 2.2 | 69.1 | 0.5 | 0.8 |
| 9 | Hf3Zn1Ce0 | 96.9 | 47.5 | 9.5 | 2.6 | 3.5 | 46 |
| 10 | Cu1Zn0.5Hf3 | 93.1 | 45.9 | 15.4 | 4.4 | 3.5 | 43 |

As shown in Table 1, in each of Experimental Examples 1 to 7 to which the present invention was applied, nitrogen could be used as a diluent gas, and butadiene and acetaldehyde as an intermediate thereof could be efficiently synthesized. Further, Experimental Examples 1 to 6 showed results even better than Example 7. Specifically, in Experimental Examples 1 to 6, the raw material conversion was 87.1 mol % or higher and the butadiene selectivity was 54.8 mol % or higher. Further, in Experimental Examples 1 to 6, the butadiene yield was 50 mol % or higher.

These results confirmed that the production efficiency of the conjugated diene can be increased by applying the present invention.

DESCRIPTION OF THE REFERENCE SIGNS

1 Reaction tube
2 Reaction bed
3 Supply pipe
4 Outlet pipe
5 Temperature controller
6 Pressure controller
10 Butadiene production apparatus

The invention claimed is:

1. A catalyst for synthesizing a conjugated diene from a raw material comprising an alcohol, which comprises, as metal elements constituting the catalyst, Ce, Zn and Hf, wherein the metal elements are supported on a porous carrier,
wherein an amount of Zn supported on the porous carrier is 0.5 to 2% by mass, with respect to 100% by mass of the porous carrier,
wherein an amount of Ce supported on the porous carrier is 0.5 to 20% by mass, with respect to 100% by mass of the porous carrier, and
wherein an amount of the Hf supported on the porous carrier is 0.5 to 10% by mass, with respect to 100% by mass of the porous carrier.

2. A method for producing a conjugated diene, comprising contacting a raw material gas containing an alcohol with the catalyst of claim 1 to obtain a conjugated diene.

3. The method according to claim 2, wherein the conjugated diene is butadiene.

4. The method according to claim 2, wherein the amount of the alcohol is 10 to 50% by volume (in terms of gas volume) with respect to 100% by volume (in terms of gas volume) of the raw material gas.

5. The method according to claim 2, wherein the raw material gas is a mixed gas of the alcohol and an inert gas.

6. The method according to claim 2, wherein the alcohol is ethanol.

7. The method according to claim 2, wherein the raw material further comprises acetaldehyde.

* * * * *